(12) United States Patent
Kosaga et al.

(10) Patent No.: US 8,809,014 B2
(45) Date of Patent: Aug. 19, 2014

(54) METHOD FOR ASSESSING THE CONDITION OF SKIN AND/OR SCALP

(75) Inventors: Masaru Kosaga, Singapore (SG); Shan He, Beijing (CN); TianGui Gong, Guangzhou (CN)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/547,206

(22) Filed: Jul. 12, 2012

(65) Prior Publication Data
US 2013/0017566 A1 Jan. 17, 2013

(51) Int. Cl.
*G01N 21/78* (2006.01)

(52) U.S. Cl.
USPC .............. 435/29; 510/130; 424/9.8

(58) Field of Classification Search
None
See application file for complete search history.

(56) References Cited

U.S. PATENT DOCUMENTS

| | | | | |
|---|---|---|---|---|
| 6,086,861 A | * | 7/2000 | Onitsuka et al. | 424/70.1 |
| 2008/0188387 A1 | * | 8/2008 | Horsewood et al. | 510/130 |
| 2011/0071123 A1 | * | 3/2011 | Schwartz et al. | 514/188 |

FOREIGN PATENT DOCUMENTS

| | | |
|---|---|---|
| CN | 101916334 | 12/2010 |
| WO | 2007026335 | 8/2007 |
| WO | 2007026340 | 8/2007 |
| WO | 2007096846 | 8/2007 |
| WO | 2010048431 | 4/2010 |

OTHER PUBLICATIONS

Pro-Clean Technical Information—Hygiena—Rapid solutions for food safety; published on Sep. 2, 2008, at the web at -www.scigiene.com/pdfs/440_PROCleanTechnicalDoc.pdf; pp. 1-3.*
Bio-Rad—Technical Note 1069—"Protein Assays—Colorimetric Protein Assays", published online on Mar. 25, 2004, pp. 1-6—at the web at http://www.bio-rad.com/LifeScience/pdf/Bulletin_1069.pdf.*
Ross et al., Videodermoscopy in the evaluation of hair and scalp disorders, J. Am. Acad. Dermatol., 2006 (published online on Apr. 16, 2006), vol. 55, pp. 799-806.*
Rosen H., A modified ninhydrin colorimetric analysis for amino acids, Archives of Biochemistry and Biophyslcs, 1957, vol. 67, pp. 10-15.*
Mu, Zhanglei, The efficacy and mechanism of 3 antifimgal shampoos in the treatment of dandruff Medicine and Health Sciences, Mar. 15, 2011, pp. 5-28.
Laden, Karl, "A Compartive Chemical Study of Dandruff Flakes, Skin Scraping and Callus" J. Soc. Cosmetic Chemists, 1965, vol. 16 pp. 491-497.
International Search Report PCT/CN2011/077069; Mailing Date Apr. 19, 2012; 12 pages.

* cited by examiner

*Primary Examiner* — Satyendra Singh
(74) *Attorney, Agent, or Firm* — Linda M. Sivik

(57) ABSTRACT

Method for assessing condition of skin and/or scalp by resulted color from the interaction of protein detecting composition with skin and/or scalp sample. Also disclosed is a method for comparing condition of different skin and/or scalp using the above method. Such conditions include, for example, skin healthiness and dandruff condition of scalp.

13 Claims, 3 Drawing Sheets

METHOD FOR ASSESSING THE CONDITION OF SKIN AND/OR SCALP

CROSS REFERENCE TO RELATED APPLICATIONS

This application claims the benefit of PCT Application No. PCT/CN2011/077,069 filed on Jul. 12, 2011.

FIELD OF THE INVENTION

In a first aspect, the present invention relates to a method for assessing condition of skin and/or scalp by resulted color from the interaction of protein detecting composition with skin and/or scalp sample. In a second aspect, the present invention relates to a method for comparing condition of different skin and/or scalp using the above method. Such conditions include, for example, skin healthiness and dandruff condition of scalp.

BACKGROUND OF THE INVENTION

Human skin and scalp become soiled due to its contact with the surrounding environment and from sebum, sweat, and so on. The soiling of skin and/or scalp causes them to have a dirty feel, and an unattractive appearance and/or smell. Such soiling of skin/scalp may cause unhealthiness, such as skin dryness. Unhealthy skin including dry skin has a less tight arrangement of stratum corneum cell layer, and tends to exfoliate more than a healthy moisture-balanced skin does. Such soiling of scalp may cause dandruff too. The soiling of the skin/scalp necessitates cleansing/shampooing with frequent regularity.

Assessing condition, especially cleanness and/or healthiness of skin/scalp is of interest in order to understand the impact of various factors including the impact of cleansing and/or shampooing. Thus, there is a need therefore for providing a method for assessing cleanness and/or healthiness of skin and/or scalp.

Furthermore, assessing dandruff condition of scalp is also of interest in order to understand the impact of various factors including the impact of shampooing and/or scalp care compositions. Thus there is also a need for providing a method for assessing dandruff condition of scalp.

SUMMARY OF THE INVENTION

The present invention relates to a method for assessing condition of skin and/or scalp comprising the steps of:
  providing at least one sample of skin and/or scalp;
  providing a protein detecting composition;
  contacting the sample with the protein detecting composition;
  assessing the sample with the protein detecting composition;
  assessing condition of the skin and/or scalp based on the color.

The present invention also relates to a method for assessing and comparing condition of skin and/or scalp comprising the steps of:
  providing at least two different samples of skin and/or scalp;
  providing a protein detecting composition;
  contacting the samples with the protein detecting compositions;
  assessing colors of the contacted compositions and/or contacted samples;
  assessing conditions of the skins and/or scalps based on the colors;
  comparing the conditions of the skins and/or scalps.

The methods allow assessing cleanness and/or healthiness of a sample of skin and/or scalp, including dandruff condition of a scalp sample.

Some methods further allow comparing conditions such as cleanness, healthiness and/or dandruff condition in different samples. Such methods are also useful for supporting advertisements about the superiority of a composition and/or a treatment versus others, in terms of its cleanness, healthiness and/or anti-dandruff effect.

BRIEF DESCRIPTION OF DRAWINGS

The patent or application file contains at least one photograph executed in color. Copies of this patent or patent application publication with color photograph(s) will be provided by the Office upon request and payment of the necessary fee.

The above-mentioned and other features and advantages of this invention, and the manner of attaining them, will become more apparent and the invention itself will be better understood by reference to the following description of embodiments of the invention taken in conjunction with the accompanying drawings, wherein.

DETAILED DESCRIPTION OF THE INVENTION

Skin and/or Scalp Sample

Figure 1:
FIG. 1 is a photo of a scalp of a person A.

The method, according to the invention, comprises the provision of at least one sample of skin and/or scalp (so-called "sample provision step"). Said samples are preferably in-vitro samples, i.e., those taken away from human. Any way can be used to collect such samples. It is preferred that, in the present invention, the sample can be taken, for example, by a cotton swab.

One sample usually comprises skin or scalp of one origin (e.g. from the same person and the same region of the body), and/or having been subjected to one cosmetic treatment.

For appropriate assessment and/or comparison, it is preferred to collect the samples in an approximately same condition. For example, when assessing condition of samples collected by cotton swabs, it is preferred to use cotton swabs with approximately same size, hardness, and to swab skin and/or scalp by such cotton swabs in approximately same way, i.e., within approximately same square centimeters, with approximately same strength, in approximately same times.

Protein Detecting Composition

The method further comprises the step of providing a protein detecting composition (so-called "composition provision step"). Any protein detecting composition can be used, as long as the composition is capable of interacting with the samples and of changing color of the composition and/or the samples. Such compositions include, for example, ninhydrin composition, bicinchoninic acid composition, biuret reagent composition, Coomassie brilliant blue G250, and mixtures thereof. Among them, preferred are those selected from the group consisting of biuret reagent composition, bicinchoninic acid composition, and mixtures thereof.

The biuret reagent compositions useful herein include, for example, water solutions containing from about 0.75% to about 1.2% of $CuSO_4.5H_2O$, and from 3% to 4.8% $KNaC_4H_4O_6.4H_2O$, and those having a pH of, preferably from about 10 to about 14, more preferably from about 12 to about 14. The Bicinchoninic Acid (BCA) compositions useful herein are water solutions containing Bicinchoninic Acid, which may be separated from the following other ingredients and mixed with them just before contacting the BCA composition with the skin/scalp samples, and $Cu^{2+}$ ion provider such as Copper Sulphate, and Sodium Carbonate, and Alkaline agent such as Sodium Hydroxide to provide high alkaline environment.

Any commercially available BCA composition can be used in this invention, such as that contained in a kit named PRO-Clean™ available from hygiena.

Contact

The method further comprises the step of contacting the samples with the protein detecting composition (so-called "contacting step").

The contacting step may be carried out by putting the samples in contact with the protein detecting composition by any suitable means and for a defined period of time sufficient for the protein detecting composition to interact with the samples. After carrying out this step, the samples and protein detecting composition may be referred hereinafter as "contacted samples" and "contacted composition" respectively.

When the protein detecting composition is provided in the form of a solution, the samples can be put in contact with the protein detecting composition by means of immersing said samples into the solution. Such means can include, for example, cotton swab-like kit comprising: a stick part storing the solution inside apart from the cotton tip; a cotton tip for collecting sample; and an initiator which can start penetration of the solution into the cotton tip.

"Defined period of time sufficient for the protein detecting composition to interact with the samples" can be varied depending on temperature and/or the protein detecting composition, for example, from 5 sec to 10 min, more preferably from 10 sec to 5 min.

When the temperature is higher and/or the ingredient level in the composition is higher in the composition, appropriate contacting period tends to be shorter. When the temperature is lower and/or the ingredient level in the composition is lower in the composition, appropriate contacting period tends to be longer. If the contacting period is too short or too long, appropriate assessment may not be able to be obtained.

For example, when assessing dandruff condition by using BCA composition contained in PRO-Clean™ available from hygiena, it is preferred that the contacting period is from about 90 sec. to about 300 sec, more preferably from about 90 sec. to about 180 sec., still more preferably from about 100 sec. to about 140 sec. at 25° C.

For example, when assessing skin healthiness by using biuret reagent composition (containing 1.2% $CuSO_4.5H_2O$, and 4.8% $KNaC_4H_4O_6.4H_2O$ and having pH of 13), it is preferred that the contacting period is from about 5 sec. to about 60 sec., more preferably from about 10 sec. to about 40 sec., still more preferably from about 15 sec. to about 30 sec. at 25° C.

Color Assessment

The method further comprises the step of assessing the color of the contacted compositions and/or contacted samples (so-called "color assessment step").

Colors can be varied, depending on the samples, protein detecting compositions and/or contacting conditions.

The step of assessing the color may be carried out using any device suitable for detecting, and if needed displaying and/or recording the color. The color may be assessed qualitatively by visual inspection, either by direct visual inspection such as observation or by indirect visual inspection such as picture analysis. Direct visual inspection comprises the step of looking at the sample, without needing any electrical measuring device. Picture analysis comprises the step of taking pictures of the samples, and analyzing the pictures by visual inspection or via a computer-aided inspection.

Kit

In the present invention, a kit can be used for making at least some of the above steps easier.

For example, a commercially available kit named "PRO-Clean™", supplied from Hygiena, contains a cotton swab, a protein detecting composition stored separately from the cotton swab, and a place to store the cotton swab before and after sampling, and activator to put the protein detecting composition into the place where the cotton swab is stored for allowing the interaction between the composition and the cotton swab after sampling.

For example, the following kit (hereinafter "health teat pen") also can be used: a kit looks like a conventional cotton swab, except that:

it has a hollow stem withholding a protein detecting composition separated from the cotton swab part; and it also has an activator to allow the composition to start penetrating into the cotton swab part.

Condition Assessment and Index

The method further comprises the step of assessing condition of skin and/or scalp by the color contacted compositions and/or contacted samples (so-called "condition assessment step"). Such conditions to be assessed herein are selected from the group consisting of skin and/or scalp leanness, skin and/or scalp health, and dandruff condition of the scalp, and mixtures thereof.

The inventors have surprisingly found that the color resulted by interaction between the protein detecting composition and skin and/or scalp samples is closely related with skin/scalp conditions such as healthiness, cleanness, and/or dandruff especially for scalp.

The condition assessment can be done by using an index which connects at least some representative skin/scalp conditions and some colors associated with each representative condition. Thus, the method may also comprise the step of providing an index to connect colors to conditions. This index can be prepared for each protein detecting compositions, depending on temperature of assessment environment and/or contacting period.

The condition assessment can be carried out using any suitable ways, for example, visual inspection containing direct visual inspection by using the index, and/or PC and its program to assess, if needed further displaying and/or recording, the condition based on the color by using the index.

For example, for assessing scalp condition, especially dandruff condition, by using the composition contained in PRO-Clean™ available from hygiene, the color can be varied from green, gray, light purple, to dark purple. In such case, the dandruff condition can be assessed, for example when allowing the contact for 120 sec. at 25° C., as follows:

When the color is green, the scalp is healthy and/or less dandruff exists on the scalp;

When the color is gray, the scalp has moderate dandruff condition; and

When the color is light to dark purple, the scalp has severe dandruff condition and/or more dandruff exists on the scalp.

For example, for assessing skin condition, especially skin healthiness, by using the biuret reagent composition (containing 1.2% $CuSO_4.5H_2O$, and 4.8% $KNaC_4H_4O_6.4H_2O$ and having pH of 13), the color can be varied from light blue, light blue-gray, light purple, to dark purple. In such case, the healthiness can be assessed, for example when allowing the contact from about 15 sec. to about 30 sec. at 25° C., as follows:

When the color is light blue, the skin is healthy and/or less scurf/germs exist on the skin;

When the color is light-blue gray or light purple, the skin has moderate scurf/germs condition; and When the color is dark purple or something close to dark purple, the skin has severe health condition and/or more scurf/germs exist on the skin.

Treatment

The method may also comprise the step of treating skin and/or scalp (so-called "treatment step"). The treatment step is preferably carried out before the sample provision step. The treatment step may be carried out by treating skin and/or scalp using any suitable cosmetic composition.

This step may be carried out by applying a cosmetic composition onto skin and/or scalp. Any suitable cosmetic composition known in the art may be used such as a hair, scalp, facial or body cleansing composition, a hair, scalp, facial or body conditioning composition, a scalp care leave-on composition, or combinations thereof. For example, for scalp, any commercially available shampoos, conditioners, scalp care leave-on treatments of tradename Pantene® and Head & Shoulders® may be used. For example, for skin, any commercially available personal cleansings of tradename Safeguard® may be used.

Only one composition may be applied onto skin and/or scalp. Alternatively, two or several compositions may be applied simultaneously or sequentially. In addition, before and/or after applying each composition, the skin and/or scalp may further be wetted, rinsed and/or dried.

Comparison

When the method comprises the step of providing at least two different samples, the method also comprises the step of comparing the conditions of the samples (so-called "comparison step"). The conditions of the sample(s) may be compared by any suitable means including, for example, visual inspection by using the index. The comparison step is beneficial, for example, for comparing the effects of untreated/treated, effect of different treatments, and/or effect of different cosmetic compositions.

The method comprises the step of providing at least two, preferably from two to four, more preferably two, different samples of skins and/or scalps. As used herein, "different samples" means samples differing from each other by origin of the skin and/or scalp, the portion of the skin and/or scalp, and/or the treatment(s) applied to the skin and/or scalp.

In one embodiment, the samples may be obtained from a different person. Alternatively, the samples may be obtained from the same person but from a different part of skin and/or scalp.

In another embodiment, one sample may comprise untreated skin and/or scalp and the other sample comprises skin and/or scalp treated with a cosmetic composition. Comparing treated samples and untreated samples is beneficial for assessing the influence of the cosmetic compositions, for example, assessing anti-dandruff benefits of the shampoo compositions on scalp.

In another embodiment, the samples may be treated with different cosmetic compositions. Comparing differently treated samples is beneficial for assessing the influence of different cosmetic compositions, for example, comparing anti-dandruff benefits of different shampoo compositions on scalp.

Advertising Step

The method may also comprise the step of utilizing said assessment to support advertising claims (so-called "advertising step"). Indeed, the present method allows correlating the condition of skin and/or scalp with the color. When advertising one treatment (e.g. body, hair or scalp cleansing composition), the data and/or the pictures obtained using this method may be used therefore support and/or demonstrate advertising claims according to which said treatment improve and/or maintain healthiness, cleanness, and/or improve or prevent dandruff.

EXAMPLE (1) Example 1

Assessment Dandruff Condition of Scalp

Materials

Scalps: Chinese female aged 17~75

Protein detecting composition: PRO-Clean™ available from hygiena

Cotton swab: PRO-Clean™ available from hygiena

Protocol

Depending on the method carried out, some of the steps may be omitted, e.g. the treating step.

1. [Sample Provision step] Each sample is prepared using the cotton swab of PRO-Clean™ available from hygiena, and swabbing one person's scalp 12 times. Each swabbing is approximately 6cm width, and conducted at different scalp portions to avoid swabbing the same scalp portions.

2. [Composition Provision step] Preparing PRO-Clean™ available from hygiena as a protein detecting composition:

3. [Contacting step] Putting the cotton swab back to PRO-Clean™ and initiating the interaction of the protein detecting composition with the sample, and allowing the contact for 120 sec. at 25° C.

4. [Color Assessment step] Assessing color of the contacted composition by direct visual inspection 5. [Condition assessment step] Assessing dandruff condition by direct visual inspection using the index detailed in the table I below.

TABLE 1

| Color | Dandruff condition |
| --- | --- |
| Green | No dandruff or Healthy scalp |
| Gray | Moderate dandruff |
| Light to Dark purple | Severe dandruff |

Assessment and Comparison of Dandruff Condition of Different Persons

Three samples of three different persons are provided. The dandruff condition is assessed according to the above material, protocol, and index. The assessment results are shown below in Table 2.

TABLE 2

Figure 2:
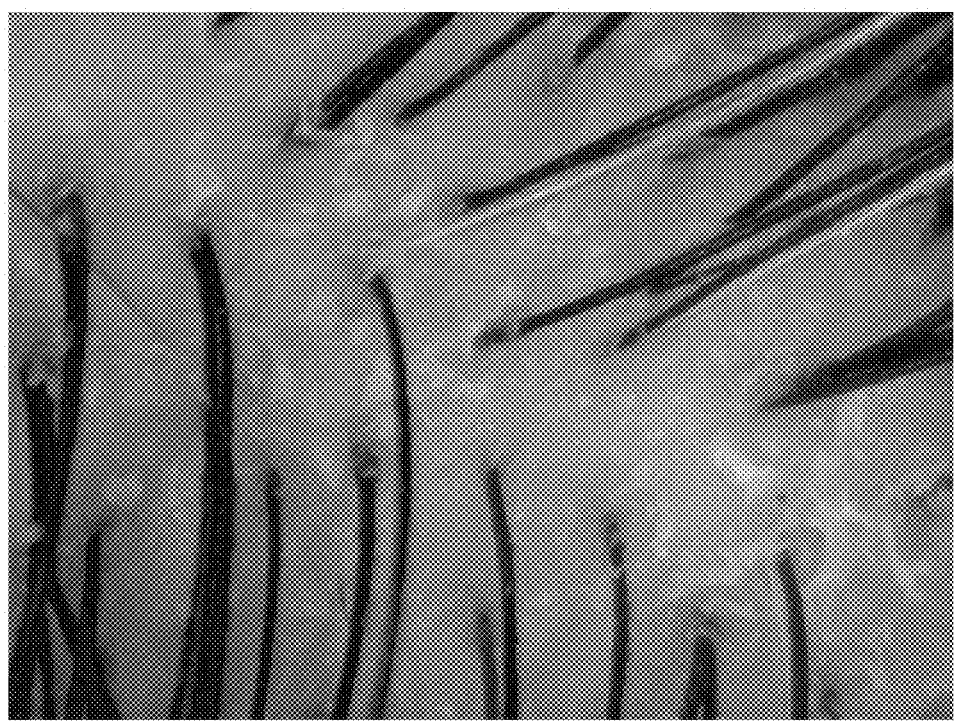
FIG. 2 is a photo of a scalp of a person B.
Figure 3:
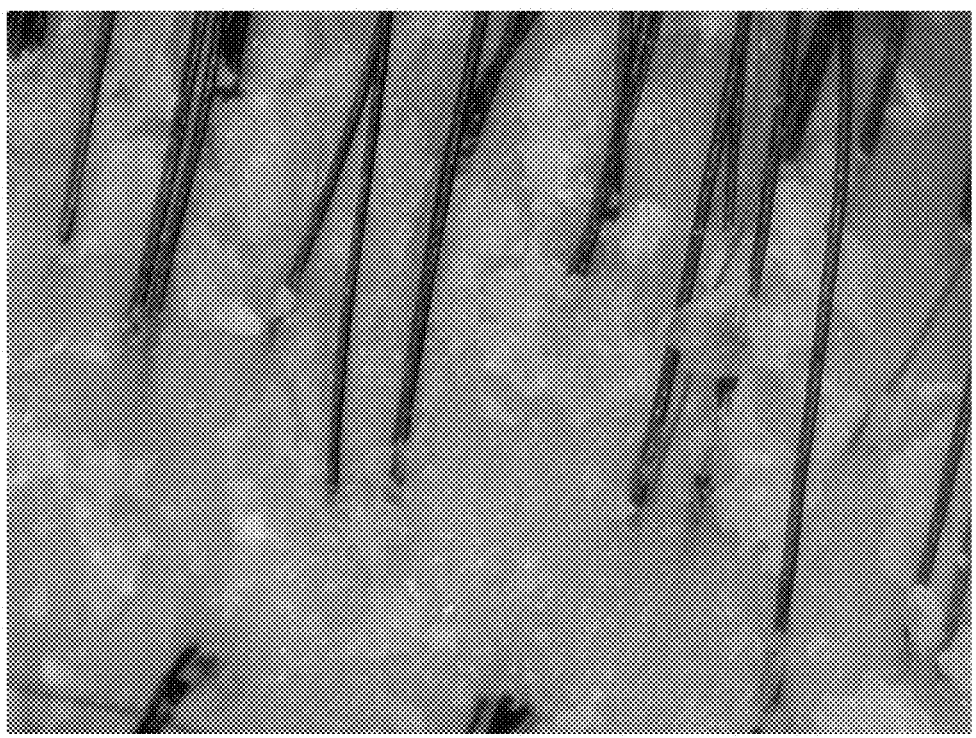
FIG. 3 is a photo of a scalp of a person C.

| Samples | Color of contacted composition | Dandruff condition based on the index | Photo of Scalp |
|---|---|---|---|
| From a person A | Green | No dandruff or Healthy scalp | FIG. 1 |
| From a person B | Gray | Moderate dandruff | FIG. 2 |
| From a person C | Light purple | Severe dandruff | FIG. 3 |

The above dandruff condition assessments based on the color are well correlated with actual conditions on the scalp, shown in FIGS. 1 to 3.

(1) Example 2

Assessment Healthiness of Skin

Materials
Skin: Elbows of Chinese female and male, aged 20~50
Protein detecting composition: Biuret reagent composition containing 1.2% $CuSO_4.5H_2O$, and 4.8% $KNaC_4H_4O_6.4H_2O$ and having pH of 13)
Cotton swab: Health test pen with cotton swab of 100% cotton, and a hollow stem having a length of 8 cm and a diameter of 0.3 cm
Cleansing composition: Safeguard body wash having the following ingredient list:

| INCI Name | % Active Ingredient Target |
|---|---|
| Aqua/Water | q.s. to 100 |
| Sodium Laureth Sulfate | 8.40 |
| Cocamidopropyl Betaine | 3.60 |
| Sodium Benzoate | 0.25 |
| Disodium EDTA | 0.10 |
| Methylchloroisothiazolinone/ Methylisothiazolinone | 0.0005 |
| Sodium Chloride | 1.30 |
| Citric Acid | 0.185 |
| STYRENE/ACRYLATES COPOLYMER | 0.288488 |
| Triclocarban | 0.005 |
| Parfum/Fragrance | 0.70 |

Percentages of compounds are weight percent per total weight of the composition.

Protocol

Depending on the method carried out, some of the steps may be omitted, e.g. the treating step.

1. [Treatment step] Skins may be treated by applying the body wash as described below, and the samples obtained from such treated skins are hereinafter referred to as "treated samples":
Place 0.5 ml body wash on the forearm of each sample; Rub the area for 15 seconds with hands; Rinse off with water for 20 seconds; and Dry the area gently by using paper tissue 2. [Sample Provision step] Swab Elbows with the health test pen for 5 times 3. [Composition Provision step] Preparing the above biuret reagent composition as the protein detecting composition.

4. [Contacting step] Initiating the interaction of the protein detecting composition with the sample, and allowing the contact for 15 to 30 seconds at 25° C.

5. [Color Assessment step] Assessing color of the cotton swab by direct visual inspection 6. [Condition assessment step] Assessing skin healthiness by direct visual inspection using the index detailed in the table 3 below.

TABLE 3

| Color | Skin healthiness condition |
|---|---|
| light blue | The skin is healthy and/or less scurf/germs exist on the skin |
| light-blue gray or light purple, | The skin has moderate scurf/germs condition |
| dark purple | The skin has severe health condition and/or more scurf/germs exist on the skin. |

Assessment and Comparison of Skin Healthiness Before/After Using Safeguard

Two samples of the same person's skin are provided. One sample is left untreated, and the other sample is treated by Safeguard. The condition is assessed according to the above material, protocol, and index. The assessment results are shown below in Table 4.

TABLE 4

Figure 4:
FIG. 4 is a photo of an elbow of one person which is left untreated.
Figure 5:
FIG. 5 is a photo of an elbow of the same person which is treated by Safeguard.

| Samples | Color | Skin Healthiness | Photo of Elbow |
|---|---|---|---|
| Untreated | Light-blue gray or Light purple | Skin has moderate scurf/germs condition | FIG. 4 |
| Treated | Light blue | Healthy and/or less scurf/germs exist on the skin | FIG. 5 |

The above skin healthiness condition assessments based on the color are well correlated with actual conditions on the skin, shown in FIGS. 4 and 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A method for assessing condition of skin and/or scalp comprising the steps of:
   providing at least one sample of skin and/or scalp;
   providing a protein detecting composition;
   contacting the skin and/or scalp sample with the protein detecting composition for a time period sufficient for the protein detecting composition to interact with the sample and produce color, wherein the protein detecting composition is selected from the group consisting of biuret reagent composition, bicinchoninic acid composition and mixtures thereof; and assessing color of the contacted skin and/or scalp sample; wherein the color of the contacted skin and/or scalp sample is associated with representative skin and/or scalp conditions as described in table 1 and/or table 3.

2. The method, according to claim 1, wherein the skin and/or scalp condition is selected from the group consisting of skin and/or scalp cleanness, skin and/or scalp health, dandruff condition of the scalp, and combinations thereof.

3. The method, according to claim 1, wherein the skin and/or scalp sample is an in-vitro sample.

4. The method, according to claim 1, wherein the color is assessed by direct visual inspection.

5. The method, according to claim 1, further comprising the step of treating the skin and/or scalp sample using a cosmetic treatment.

6. The method, according to claim 5, wherein the cosmetic treatment is selected from the group consisting of a hair, scalp, facial or body cleansing composition; a hair, scalp, facial or body conditioning composition; a scalp care leave-on composition; and combinations thereof.

7. The method, according to claim 1, further comprising the step of utilizing said assessment to support advertising claims about the efficacy of a cosmetic treatment.

8. A method for assessing and comparing condition of skin and/or scalp comprising the steps of:

providing at least two different samples of skin and/or scalp;

providing a protein detecting composition, wherein the protein detecting composition is selected from the group consisting of biuret reagent composition, bicinchoninic acid composition and mixtures thereof;

contacting the samples with the protein detecting compositions for a time period sufficient for the protein detecting composition to interact with the samples and produce color;

assessing colors of the contacted skin and/or scalp samples;

wherein the colors of the contacted skin and/or scalp samples are associated with representative skin and/or scalp conditions as described in table 1 and/or table 3; and comparing the conditions of the skins and/or scalps.

9. The method, according to claim 8, wherein the samples differ from each other by the origin of the skin and/or scalp, the portion of the skin and/or scalp, and/or the treatment(s) applied to the skin and/or scalp.

10. The method, according to claim 9, wherein one sample comprises untreated skin and/or scalp and the other sample comprises skin and/or scalp treated with a cosmetic composition.

11. The method, according to claim 10, further comprising the step of utilizing said assessment and comparison to support advertising claims about the efficacy of a treatment versus non-treatment.

12. The method, according to claim 8, wherein the samples are treated with different cosmetic treatments.

13. The method, according to claim 12, further comprising the step of utilizing said assessment and comparison to support advertising claims about the superiority of one cosmetic treatment versus the other.

* * * * *